United States Patent [19]

Rock et al.

[11] 4,122,841
[45] Oct. 31, 1978

[54] PROBE TIP

[75] Inventors: Erwin H. Rock, Dobbs Ferry; Irwin Klar, New City, both of N.Y.

[73] Assignee: American Electromedics Corporation, Acton, Mass.

[21] Appl. No.: 807,591

[22] Filed: Jun. 17, 1977

Related U.S. Application Data

[63] Continuation of Ser. No. 647,752, Jan. 9, 1976, abandoned.

[51] Int. Cl.² .......................... A61B 10/00; A61B 5/12
[52] U.S. Cl. .................................... 128/2 Z; 128/151
[58] Field of Search ................ 128/2 K, 2 Z, 9, 151, 128/152; 179/1 N

[56]  References Cited
U.S. PATENT DOCUMENTS

| | | | |
|---|---|---|---|
| 2,437,490 | 3/1948 | Watson et al. | 128/152 |
| 2,458,884 | 1/1949 | Volkmann | 128/152 |
| 2,717,596 | 9/1955 | Knight | 128/152 |
| 2,888,921 | 6/1959 | Nielson et al. | 128/151 |
| 3,131,241 | 4/1964 | Mendelson | 128/151 X |
| 3,415,246 | 12/1968 | Hill | 128/152 |
| 3,618,600 | 11/1971 | Douglass | 128/152 |
| 3,800,791 | 4/1974 | Visor | 128/152 |
| 3,882,848 | 5/1975 | Klar et al. | 128/2 Z |

*Primary Examiner*—Kyle L. Howell
*Attorney, Agent, or Firm*—Holland, Armstrong, Wilkie & Previto

[57] ABSTRACT

A tip for an ear test probe is disclosed for use in clinical evaluations of hearing problems. There are a number of important tests for evaluating hearing system losses which are based upon measurements taken in patients' external ear canals using a probe which uses a tip to seal the ear canal. An improved tip is described for such tests. The tip has an improved curved flange structure which helps to insure perfect sealing of the ear canal without requiring precise probe positioning or high probe sealing pressures.

1 Claim, 4 Drawing Figures

PROBE TIP

This is a continuation of application Ser. No. 647,752 filed Jan. 9th, 1976 and now abandoned.

BACKGROUND OF THE INVENTION

The present invention relates to clinical evaluation of hearing loss and more particularly to an improved probe tip for use with ear test equipment.

There is a test procedure for evaluating hearing losses and/or ear disease, for example, which is known as Acoustic Impedance Testing or Impedance Audiometry. The test uses acoustical measurements made within the patient's outer ear canal and includes the step of closing off the ear canal adjacent to the patient's tympanic membrane with a probe. The probe has a tip to form an air seal for permitting the control of the air pressure within the sealed cavity and the transmission to and receipt of sound signals from the closed cavity. Several other hearing tests use probes with tips.

The equipment for these tests has been used heretofore with a number of ear probe tips for forming the seals. The probe tip of the present invention is improved whereby it forms a better and more sure seal permitting the tests to be done quickly and conveniently without critical adjustments of the probes or of the probe supports. This is of particular value in the case of children and certain other patients who may have short attention span or an inability to cooperate in the test procedures.

Accordingly, an object of the present invention is to provide improved probe tips for clinical evaluations of hearing losses or other ear problems.

Another object of the present invention is to provide an improved probe tip of more efficient form for providing better sealing and for use with various probe supports including hand held probes and others. It likewise eliminates losing or displacing the tip within the external auditory canal.

Other and further objects of the invention will be obvious upon an understanding of the illustrative embodiment about to be described or will be indicated in the appended claims, and various advantages not referred to herein will occur to one skilled in the art upon employment of the invention in practice.

BRIEF DESCRIPTION OF THE DRAWING

A preferred embodiment of the invention has been chosen for purposes of illustration and description and is shown in the accompanying drawing forming a part of the specification, wherein.

DESCRIPTION OF THE PREFERRED EMBODIMENT

This invention relates particularly to an improved probe tip for use in performing a number of tests in connection with a clinical evaluation of hearing losses or other problems. The following description will refer to typical tests in a general way, particularly with reference to FIGS. 2 and 3 to provide a background for the description of the elements of the tip and its improved features as used on a typical probe. The tip is particularly useful with a hand held probe, for example, as used in acoustic impedance tests in the setup illustrated diagrammatically in FIG. 1. The tip is also useful with a variety of differing probes and probe mountings including head bands.

Figure 2:
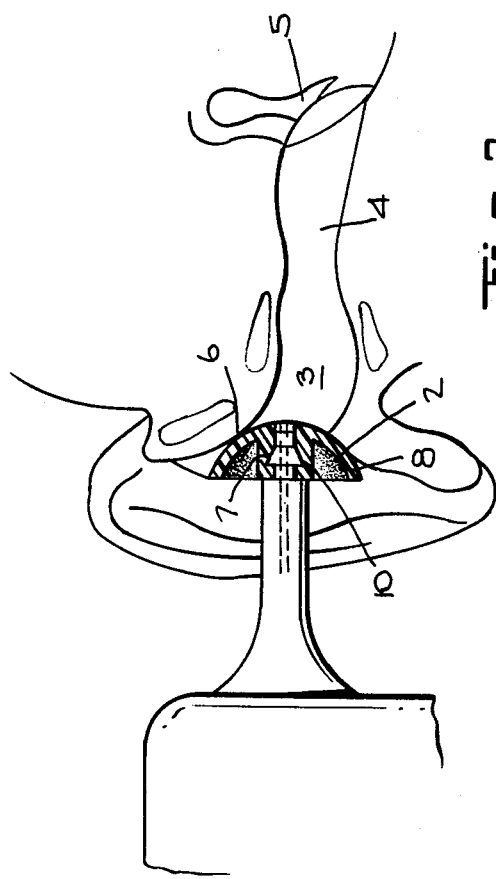
FIG. 2 is a vertical sectional view of the probe tip in test position.
Figure 3:
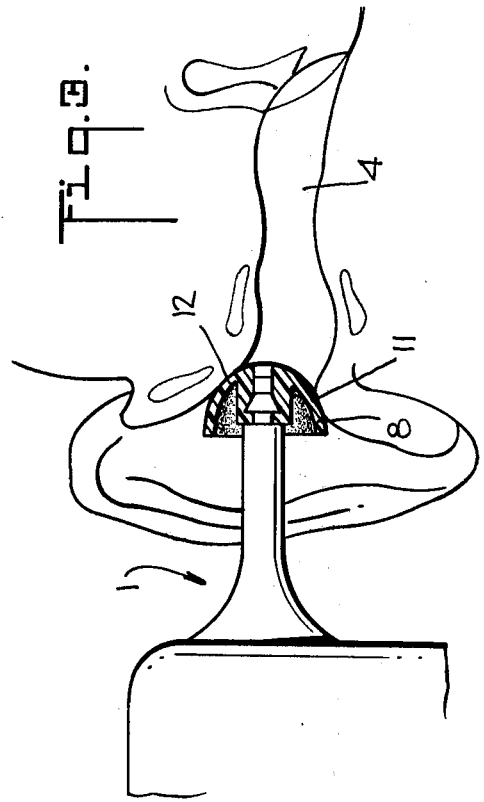
FIG. 3 is a vertical sectional view of the probe tip corresponding to FIG. 2 but with the probe differently positioned.
Figure 1:
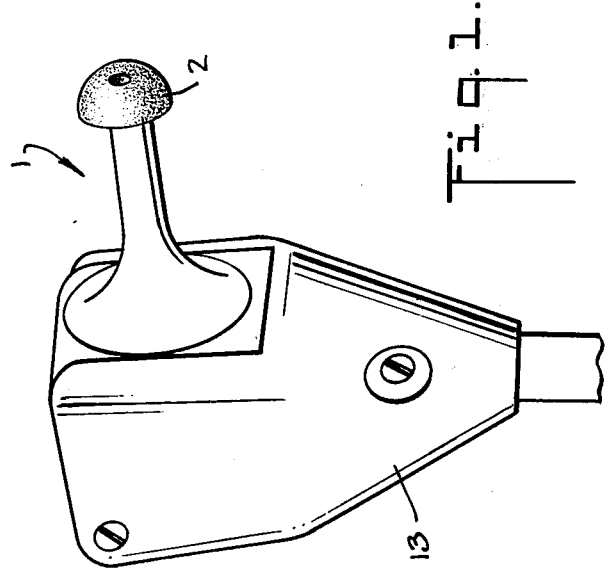
FIG. 1 is a perspective view of a preferred embodiment of the tip in position on a hand held probe.

FIG. 1 illustrates one form of a hand held probe for use with test equipment for a test known as Tympanometry. This test uses a probe 1 with a tip 2 in accordance with the invention to form a closed-off cavity 3 within the patient's ear canal 4. FIGS. 2 and 3 illustrates a probe 1 equipped with a tip 2 in accordance with the present invention held at the patient's ear canal 4 so that the tip 2 closes off and hermetically seals the cavity 3 adjacent to the ear tympanic membrane 5. The resilient cuff or tip 2 on the ear probe 1 is positioned on the inner end of the probe 1 for forming the air-tight or hermetic seal with the canal 4 walls at a generally ring-like area 6.

The tympanometric test provides for the transmission of a sound signal wave of a predetermined frequency and volume through the probe 1 to the sealed-off cavity 3. The testing involves the supply of this sound signal to the cavity 3 with the tympanic membrane 5 being stressed or conditioned by the adjustment of the air pressure within the sealed cavity 3. The tympanometric measurements are made for determining ear drum compliance changes as the air pressure is altered within the sealed cavity 3.

Probes 1 also are used in a generally similar way with sealed ear canals for Static Compliance Testing and for Acoustic Reflex Threshhold tests. In the Static Compliance Test, which measures the middle ear sytem mobility, a condition of the testing also requires a setting and an adjustment of air pressure within the sealed-off ear canal 4.

The Improved Probe Tip

Figure 4:
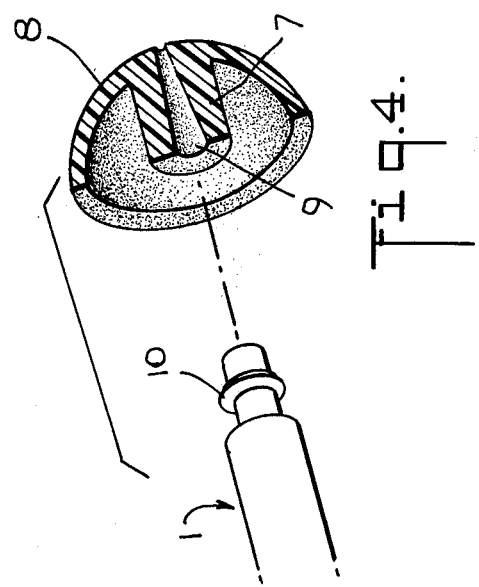
FIG. 4 is an exploded perspective view of the probe tip and a supporting probe end.

The improved tip 2 will now be described in detail with reference to the drawing. As illustrated in the drawing, the tip 2 comprises a central support portion 7 adapted for engagement with the end of the rigid probe member 1. The tip has a rounded convex skirt or flange 8 projecting from the inner end of the central support portion 7. The improved tip 2 is preferably formed of a soft resilient material such as latex, silicon or a plastic resin with a corresponding softness and resiliency. The support portion 7 includes a central aperture 9 which preferably has a cross-section of increasing size outwardly of the support 7 of the general form illustrated in FIG. 4 for facilitating the application of the tip 2 to the probe 1 and for firmly retaining the tip 2 in place on the probe 1 during testing. This portion of the tip 2 fits into locking engagement with a lock or gripping flange 10 on the inner end of the hollow metallic or other rigidly formed probe 1.

The convex and projecting flange 8 preferably has a rounded shape as substantially as illustrated. This mushroom-like shape together with the relatively thin cross-section and flexible nature of the material results in the formation of a tight seal between the outer surface of the probe flang 8 and the walls of the ear canal 4 under test.

A tight seal is obtained regardless of the precise alignment of the probe with respect to the opening in the ear canal 4. FIG. 2, for example, illustrates the probe 1 being aligned with an essentially axial alignment with the ear canal 4 and with a seal being provided more or less uniformly around a ring-like area 6 on the flange tip 2.

FIG. 3 illustrates a seal being formed even where the probe 1 may be presented to the ear canal 4 at an angle. In this case, a seal is formed on an outer portion 11 of the flange 8 on one side of the tip 2 and at a more centrally positioned area 12 of the flange 8 on an opposite section of the tip 2.

This sealing capability permits a tight seal to be made for satisfactory testing without requiring precise positioning of the test probe 1 and without requiring the application of substantial forces on the probe 1. This makes the new tip 2 particularly useful for a variety of test instruments including a hand held probe 13 which may have the general form illustrated in FIG. 1.

A hand held probe is applied to the ear of the patient under test while being held in the clinician's hand. The improved tip 2 facilitates such a hand held operation as it permits a seal to be made without difficult or cirtical probe alignment being required to establish or to maintain the desired ear canal air pressure.

The improved sealing capacity of the tip 2 alos adapts it for use with other probes including those mounted on adjustable head bands as it also eliminates the need for any critical positioning of the probes on the bands during the testing.

It will be seen that an improved probe tip has been provided which is adapted for hand held use and other uses and which thereby provides for fully satisfactory acoustic testing of a patient's hearing with a decrease in the manipulations required by the clinician. This results in a reduction in the required test time as well as providing increased comfort for the patient being tested.

As various changes may be made in the form, construction and arrangement of the parts herein without departing from the spirit and scope of the invention and without sacrificing any of its advantages, it is to be understood that all matter herein is to be interpreted as illustrative and not in a limiting sense.

Having thus described our invention, we claim:

1. In an improved replaceable and resilient and compressible tip for a test probe for forming an air tight seal between the probe and the ear canal of an ear being tested and having a central support portion with an elongated probe mounting aperture extending through said support portion the improvements comprising said aperture flaring outwardly toward one end of the support portion, a flange projecting radially outwardly from the other end of said support portion, said flange having a convex outer surface for engaging a ring-like area on the wall of the entrance to the outer ear canal to form the seal and having a concave inner surface generally parallel to said convex outer surface and cooperating to form a C-shaped flange of uniform cross-section with the flange edge being the radially outermost portion of the tip, and said support portion and said flange having generally equal dimensions parallel to the elongated probe mounting aperture.

* * * * *